US008778702B2

(12) United States Patent  
Markwort et al.

(10) Patent No.: US 8,778,702 B2
(45) Date of Patent: Jul. 15, 2014

(54) METHOD OF INSPECTING AND PROCESSING SEMICONDUCTOR WAFERS

(75) Inventors: Lars Markwort, Haimhausen (DE); Reza Kharrazian, Stephanskirchen (DE); Christoph Kappel, Aschheim (DE); Pierre-Yves Guittet, München (DE)

(73) Assignee: Nanda Technologies GmbH, Unterschleissheim (DE)

( * ) Notice: Subject to any disclaimer, the term of this patent is extended or adjusted under 35 U.S.C. 154(b) by 97 days.

(21) Appl. No.: 13/390,676

(22) PCT Filed: Aug. 16, 2010

(86) PCT No.: PCT/EP2010/005026
§ 371 (c)(1),
(2), (4) Date: Feb. 15, 2012

(87) PCT Pub. No.: WO2011/020589
PCT Pub. Date: Feb. 24, 2011

(65) Prior Publication Data
US 2012/0142122 A1   Jun. 7, 2012

(30) Foreign Application Priority Data

Aug. 17, 2009 (EP) .................................. 09010570

(51) Int. Cl.
*H01L 21/00* (2006.01)
*H01L 21/66* (2006.01)
*G01N 21/00* (2006.01)

(52) U.S. Cl.
USPC ............................... 438/7; 438/16; 356/237.2

(58) Field of Classification Search
None
See application file for complete search history.

(56) References Cited

U.S. PATENT DOCUMENTS

| | | | |
|---|---|---|---|
| 5,583,632 A | 12/1996 | Haga | |
| 5,763,123 A | 6/1998 | Shishido et al. | |
| 6,813,032 B1 * | 11/2004 | Hunter | 356/601 |
| 2005/0280808 A1 | 12/2005 | Backhauss et al. | |
| 2006/0066843 A1 | 3/2006 | Guetta et al. | |
| 2008/0243412 A1 | 10/2008 | Horie et al. | |
| 2010/0007958 A1 | 1/2010 | Anderson et al. | |

FOREIGN PATENT DOCUMENTS

| | | |
|---|---|---|
| EP | 1 860 428 A2 | 11/2007 |
| EP | 1 860 428 A3 | 11/2007 |
| JP | H07-202430 A | 8/1995 |
| JP | H08-005571 A | 1/1996 |
| JP | 2002-195956 A | 7/2002 |
| JP | 2007-147376 A | 6/2007 |

(Continued)

OTHER PUBLICATIONS

International Search Report and Written Opinion mailed on Dec. 9, 2010 for PCT Application No. PCT/EP2010/005026 filed on Aug. 16, 2010, 9 pages.
Machine Translation in English of Abstract for JP 2002-195956 visited at www.espacenet.com on May 27, 2014, 2 pages.
Machine Translation in English of Abstract for JP 2007-303904 visited at www.espacenet.com on May 27, 2014, 2 pages.
Machine Translation in English of Abstract for JP 2007-147376 visited at www.espacenet.com on May 27, 2014, 2 pages.
Machine Translation in English for JP 2002-195956 visited at http://www.ipdl.inpit.go.jp/homepg_e.ipdl on May 27, 2014, 15 pages.
Machine Translation in English for JP 2007-303904 visited at http://www.ipdl.inpit.go.jp/homepg_e.ipdl May 27, 2014, 44 pages.
Machine Translation in English for JP 2007-147376 visited at http://www.ipdl.inpit.go.jp/homepg_e.ipdl on May 27, 2014, 13 pages.

*Primary Examiner* — Scott B Geyer
(74) *Attorney, Agent, or Firm* — Silicon Valley Patent Group LLP

(57) ABSTRACT

A wafer inspection method comprises imaging a full surface of the wafer at an imaging resolution insufficient to resolve individual microstructures which are repetitively arranged on the wafer. A mask 109 is applied to the recorded image and unmasked portions 111 of the image are further processed by averaging. The unmasked portions 111 are selected such that they include memory portions of the wafer.

41 Claims, 12 Drawing Sheets

(56) References Cited

FOREIGN PATENT DOCUMENTS

| | | |
|---|---|---|
| JP | 2007-303904 A | 11/2007 |
| JP | 2008-249386 A | 10/2008 |
| WO | WO 2007/088542 A2 | 8/2007 |
| WO | WO 2007/088542 A3 | 8/2007 |
| WO | WO 2008/152801 A | 12/2008 |
| WO | WO 2009/024978 A2 | 2/2009 |
| WO | WO 2009/024978 A3 | 2/2009 |
| WO | WO 2011/020589 A1 | 2/2011 |

\* cited by examiner

METHOD OF INSPECTING AND PROCESSING SEMICONDUCTOR WAFERS

CROSS-REFERENCE TO RELATED APPLICATIONS

This application is the National Stage of International Patent Application No. PCT/EP2010/005026, filed Aug. 16, 2010, which, in turn, claims the benefit of European Patent Application No. 09 010 570.1, filed Aug. 17, 2009, both of are incorporated herein by reference.

BACKGROUND

1. Field

The present disclosure relates to methods of processing and inspecting semiconductor wafers.

2. Brief Description of the Related Art

A miniaturized devices, such as a semiconductor devices, are manufactured by applying a plurality of processing steps to a semiconductor wafer. The processing may include a film forming processing to provide a resist layer on the substrate, an exposure processing to expose portions of the resist, a post-exposure bake processing, a development processing, an etching processing to etch exposed or non-exposed portions of the resist, a deposition processing to deposit material at exposed or non-exposed portions of the resist, and other suitable processings. The processings are controlled using suitable processing parameters, such as temperatures, concentrations, exposure doses and other settings. In view of a high throughput of the manufacture it is necessary to control each of the processings based on corresponding parameters such that a desired result is achieved at each processing. Inspection of the semiconductor wafer can be performed after one or more of the applied processings. Based on an inspection result it is possible to adjust one or more of the processing parameters.

The inspection can be performed using suitable inspection tools to measure various properties of the semiconductor wafer and of microstructures formed thereon. Some inspection tools use optical methods for inspecting the wafer and may generate images of the wafer which can be further analyzed to confirm that the processing is performed as desired or to determine defects in the processed wafer. Optical inspection tools are generally divided into micro-defect inspection tools and macro-defect inspection tools.

Micro-defect inspection tools aim to detect deficiencies in the smallest manufactured microstructures having dimensions of 0.1 µm and below. An advantage of micro-defect inspection tools is that a geometry or other properties of a microstructure can be directly verified and that deficiencies in these microstructures can be directly shown. A disadvantage of micro-defect inspection tools is the long time needed for inspection and the high amount of generated data which have to be processed if the whole surface of the substrate is to be inspected. If only portions of the surface of the substrate are inspected due to time considerations, there is a risk that certain deficiencies are not detected.

Macro-defect inspection tools aim to achieve a high throughput at the cost of a lower sensitivity to defects and at lower spatial resolution of the generated images. Macro-defect inspection tools have an advantage in that large portions of the substrates or the complete substrates can be inspected within a short time, and they have a disadvantage in that the smallest manufactured microstructures are not directly imaged to detect deficiencies in those microstructures.

It is desirable to extend the applicability of macro-inspection tools and to obtain more detailed inspection information from a semiconductor wafer with a high throughput.

It is further desirable to use information obtained using a macro-defect inspection tool in a manufacturing process of semiconductor wafer.

SUMMARY

The present disclosure provides methods of inspecting a semiconductor wafer which allow to obtain valuable information about microstructures formed on the semiconductor wafer.

The semiconductor wafer may include a plurality of different regions in which microstructures are arranged according to different arrangement patterns. For example, microstructures can be arranged in a regular repetitive arrangement pattern, such that a repetition period can be identified for the arrangement in one or two directions. There can be different regions having different arrangement patterns having different repetition periods. Moreover, other regions may have arrangements of microstructures which are irregular or random.

In some embodiments, the disclosure provides an imaging of at least a portion of the semiconductor wafer onto an array of pixels of a detector. The imaging may include optical imaging, using imaging rays of light.

In certain embodiments, the disclosure provides for using light of a broad spectral range for the imaging. The spectral range may comprise visible light, infrared light and ultraviolet light.

In other certain embodiments, the disclosure provides for using light of a narrow spectral range for the imaging. The narrow spectral range may be within visible light, infrared light or ultraviolet light.

In certain embodiments, the imaging is performed using an optical system comprising lenses and/or mirrors.

In some embodiments, the disclosure provides an imaging such that an area of the semiconductor wafer which is imaged onto one pixel of the detector has an extension of more than five times, more than ten times or more than fifty times of a smallest repetition period at which microstructures are arranged in a region. This means that it is not possible to observe or detect a geometry or structure of the microstructures formed in those regions using the detector with the array of pixels. In other words, the microstructures are too small to be directly observed using the imaging. However, a selected region in which the microstructures are arranged according to a same regular repetitive arrangement pattern is imaged onto a selected group of plural pixels of the detector.

In some embodiments, the disclosure provides for imaging of a selected region onto a group of more than 5 pixels, more than 10 pixels, more than 25 pixel or more than 35 pixels. For example, a selected region can be imaged onto a group of 3×3 pixels, 4×4 pixels, 5×5 pixels, 3×7 pixels, 5×6 pixels and so on. Moreover, the groups of pixels do not need to occupy rectangular portions of the detector; the groups of pixels can have arbitrary shapes substantially corresponding to the shapes of the selected regions on the wafer.

In some embodiments, the disclosure provides for collecting detection signals from pixels of a detector and calculating values from selected detection signals. Among the detection signals available from all pixels of the detector, only selected detection signals are used for calculation of the values, and other detection signals are not used for or excluded from the calculation of those values. In other words, some pixels are "masked" in that sense that detected intensities from those signals do not influence a result of the calculation of the plural values. The detection signals which do not influence the calculation result include detection signals from pixels which are not members of any of those selected groups of pixels onto which selected regions of the wafer are imaged, wherein the selected regions are those regions in which microstructures are arranged according to a regular repetitive arrangement pattern. Detection signals which influence the calculation result comprise detection signals from the selected groups of pixels onto which the selected regions are imaged.

In some embodiments, the disclosure provides for determining a feature property of the microstructures formed in at least one selected region of the wafer, which region is imaged onto a group of pixels providing detection signals used for calculating at least one value corresponding to the imaged selected region. In certain embodiments, the feature property comprises a line width, a side wall angle, a height, a footing, an undercut, a corner rounding and a critical dimension (CD), an overlay shift and a layer thickness of the microstructures arranged in the selected region. It may be possible to determine properties of features of microstructures even though the microstructures can be not directly resolved in the imaging.

In certain embodiments, the semiconductor wafer includes a plurality of dies, wherein a die is a small block of semiconducting material, on which a given functional circuit is fabricated. Each die may include at least one selected region in which microstructures are arranged according to a regular repetitive arrangement pattern.

In some embodiments, the disclosure provides a method of processing a semiconductor wafer using at least one process parameter, and wherein the at least one process parameter is changed based on at least one value determined from detection signals collected from pixels of a detector onto which regions of the semiconductor wafer processed according to the at least one process parameter is imaged.

In some other embodiments the processing comprises a deposition, such as a chemical vapor deposition (CVD) and a physical vapor deposition (PVD), wherein the at least one process parameter comprises a concentration, a temperature and a duration.

In certain embodiments, the disclosure provides a processing comprising exposing of a substrate with a pattern, wherein the at least one process parameter comprises an exposure dose and/or a focus used in the exposing.

In some embodiments, a processing of a substrate comprises etching of the substrate, wherein at least one process parameter comprises an etch time, an etch temperature and a concentration of a medium used in the etching.

According to embodiments, a method of manufacturing a semiconductor wafer comprises coating the wafer with a resist; exposing a pattern onto the resist after the coating; developing the patterned resist after the exposing; etching the wafer through the developed resist after the developing; and removing the resist remaining on the wafer after the etching; wherein an inspection of the wafer is performed after the etching of the wafer and before the removing of the remaining resist. The removing of the remaining resist may comprise a processing of ashing to burn off a remaining resist polymer, and a subsequent step of cleaning to remove residue and resist particles.

According to some embodiments, a method of manufacture of a semiconductor wafer includes inspecting the semiconductor wafer, wherein the inspecting comprises: positioning the wafer relative to an imaging optics and a camera such that the wafer is imaged onto the camera by the imaging optics; directing illuminating light produced by a light source onto the wafer; providing a first light setting and recording a first image of the wafer with the camera using illuminating light reflected from the wafer; and providing a second light setting and recording a second image of the wafer with the camera using illuminating light reflected from the wafer; wherein the first and second light settings differ with respect to at least one of a polarization and a spectrum of the light used for imaging the wafer onto the detector.

According to some embodiments, the first and second light settings are produced by of at least one optical filter provided in at least one of a beam path between the light source and the wafer and a beam path between the wafer and the camera, wherein the optical filter can be changed to such that a polarization of the light traversing the filter changes and/or such that a spectral distribution of intensities of the light traversing the filter changes.

According to some embodiments, the first and second light settings are produced by changing a light source generating the illumination light. For example plural light sources, such as plural LEDs, providing different spectral ranges of illumination light can be provided and selectively operated to selectively generate illumination light of different spectral distributions.

According to exemplary embodiments herein, even more than two images can be recorded at more than two light settings.

According to further exemplary embodiments herein, the inspecting can be performed according to a method illustrated above and involve calculating, for each recorded image, a value for a group of pixels of the respective image.

According to other exemplary embodiments herein, an image processing is applied to the recorded images to calculate a new image based on the recorded images, wherein at least one value is calculated for one or more groups of pixels of the new calculated image.

With such methods using more than one image of a same wafer recorded at different light settings it is possible to obtain information relating to the wafer which could not be obtained from a single image recorded at a single light setting.

According to exemplary embodiments, a position of the wafer relative to the imaging optics and camera is maintained constant between the recording of the first image and the recording of the second image, such that an image processing applied to the plural recorded images is facilitated and that results of image processing can be readily associated with particular locations and regions of the wafer.

According to some embodiments, the light with which the first image is recorded has a first spectral distribution and the light with which the second image is recorded has a second spectral distribution, and wherein the first and second light settings are configured such that a central wavelength of the first spectral distribution differs from a central wavelength of the second spectral distribution by more than 50 nm or more than 100 nm. The central wavelength can be calculated according to one of the methods known in the art. For example, the central wavelength can be calculated by determining a center of gravity of an area below a graph representing the spectral distribution of the light used.

According to some embodiments, a width of each of the first and second spectral distributions is smaller than 100 nm or smaller than 50 nm. The width of the spectral distribution can be calculated according to one of the methods known in the art. For example, the width of the spectral distribution can be calculated by determining upper and lower bounds of a portion of the spectral distribution such that, for example, 90% of the spectral intensity are contained within a wavelength range defined by the upper and lower bounds. The difference between the upper bound and the lower bound will then represent the width of the spectral distribution.

According to exemplary embodiments herein a wavelength of 430 nm is within a width of the first spectral distribution and/or wherein a wavelength of 650 nm is within a width of the second spectral distribution.

Such selection of wavelength can of advantage in obtaining information relating to structures located below a surface of the inspected wafer. The image recorded using the shorter wavelength light will contain information mainly relating to structures located close to the surface of the wafer due to a limited penetration depth of the short wavelength light. The image recorded using the longer wavelength light will contain information relating to structures located close to the surface and to structures located a certain distance below the surface of the wafer due to the greater penetration depth of the longer wavelength light. It is possible to calculate a new image by applying mathematical operations to pixel intensities of corresponding pixels of the two images to obtain pixel intensities for the pixels of the new image. With mathematical operations selected depending parameters such as the light settings and exposure condition of the recorded images it is possible to reduce the information relating to the structures located close to the surface in the calculated image such that the calculated image mainly contains information relating to the structures located a distance below the surface.

According to other embodiments, the light with which the first image is recorded has a first polarization direction and the light with which the second image is recorded has a second polarization direction, and wherein the first and second light settings are configured such that the first polarization direction differs from the second polarization direction by more than 10°, by more that 20° or by more than 40°. Herein, it is possible that the light is only partially polarized since a perfect linear polarization of 100% is difficult to obtain in practice. Moreover, according to further embodiments, the first polarization differs from the second polarization with respect to a degree of polarization. For example, the first image can be recorded using non-polarized light while the second image is recorded using light having a degree of polarization of, for example 60%.

According to some embodiments, the light setting is changed by changing a filter provided in an illumination beam path of an inspection system. According to other embodiments, the light setting is changed by changing a filter provided in an imaging beam path of an inspection system, and according to still further embodiments, the filter setting is changed by changing both a filter provided in an illumination beam path of an inspection system and a filter provided in an imaging beam path of the inspection system. The changing of the filter may include replacing a first filter having a first transmission characteristics positioned in the beam path with a second filter having a second transmission characteristics. The transmission characteristics may differ with respect to a spectral distribution of intensities and/or with respect to a polarization of the light transmitted trough or reflected from the filter.

According to some other embodiments, the light setting is changed by changing a light source generating the illumination light in an illumination beam path of an inspection system.

In some embodiments, the disclosure provides a method of imaging at least a portion of a substrate onto a detector. According to some embodiments herein, the complete surface of the substrate is imaged onto the detector.

In some embodiments, the disclosure provides a method of inspecting a semiconductor wafer, wherein at least a portion of the wafer is imaged onto a detector and wherein the imaging is a telecentric imaging such that a variation of chief rays of an imaging beam path is less than 5°, in particular less than 3°, across the portion of the wafer which is imaged onto the detector.

In some embodiments, the disclosure provides a method of illuminating a semiconductor wafer to be imaged, wherein the illuminating is a telecentric illuminating such that a variation of chief rays of an illuminating beam path is less than 5°, in particular less than 3°, across a region of the wafer which is imaged.

BRIEF DESCRIPTION OF THE DRAWINGS

The foregoing as well as other advantageous features of the disclosure will be more apparent from the following detailed description of exemplary embodiments, the drawings and the claims.

DETAILED DESCRIPTION OF EXEMPLARY EMBODIMENTS

Figure 1:
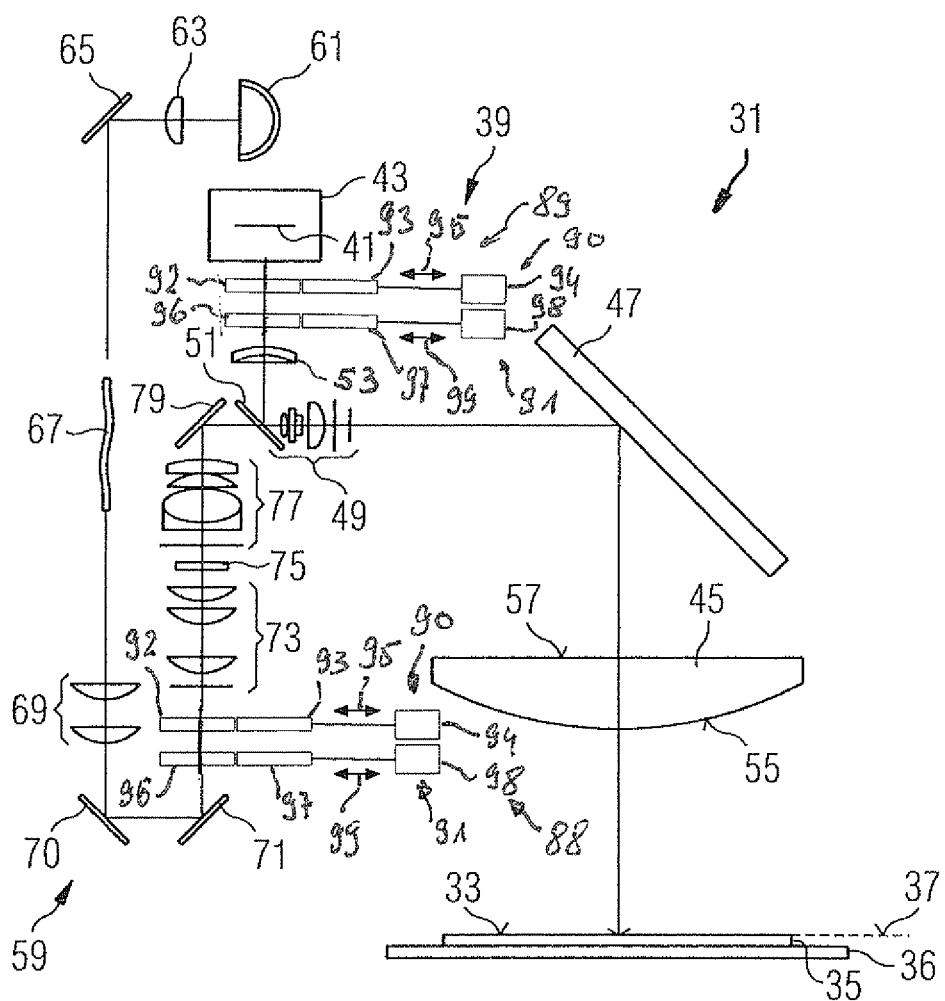
FIG. 1 is a schematic illustration of a macro-defect inspection system.

In the exemplary embodiments described below, components that are alike in function or in structure are generally designated by like reference numerals.

FIG. 1 is a schematic illustration of a macro-defect inspection system 31.

The system 31 is designed to obtain images of surfaces 33 of semiconductor wafers 35. In this example, the wafers 35 are wafers currently used in semiconductor manufacturing having a diameter of about 200 mm or about 300 mm. However, the embodiment is not limited to such wafer diameters and can be applied to other wafer diameters, such as 400 mm or more. Moreover, the embodiments illustrated herein below are generally applicable to inspection of substrates which are different from semiconductor wafers and include objects such as data carriers, biological samples, chemical processing systems and so on.

The wafer 35 is mounted on an object support 36 such that its surface 33 is disposed in an object plane 37 of an imaging beam path 39 of the system 31. The imaging beam path 39 is configured and arranged to image the full surface 33 of the wafer 35 onto an array 41 of pixels of an image detector 43. For this purpose, the imaging beam path 39 comprises an objective lens 45, a folding mirror 47, a first lens group generally indicated at 49, a beam splitter 51, a second lens group generally indicated at 53 and the radiation sensitive surface 41 of the image detector 43. The imaging beam path 39 is telecentric on the side of the object plane 37 and it can also be telecentric on the side of its image plane which coincides with the array 41 of pixels. Due to the telecentric property on the side of the object plane 37, a diameter of the objective lens 45 is greater than the diameter of the wafer surface 33. However, in examples where the telecentric property on the side of the object plane 37 is not required, it is possible to use objective lenses of a reduced diameter.

While the objective lens 45 has positive optical power, the lens group 49 has negative optical power, the lens group 53 has positive optical power, and the beam splitter 51 is disposed in a space between the first and second lens groups 49, 53.

The example of the system 31 illustrated in FIG. 1 further comprises optical filter 89 positioned in the imaging beam path extending from the wafer 35 to array 41 of pixels of the detector 43. In the illustrated example, the optical filter 89 comprises a polarization filter 90 and a spectral filter 91. The optical filter 89 can be used to select properties of the light used for the imaging of the wafer onto the array of pixels.

The polarization filter 90 comprises two filter plates 92 and 93 which can be selectively placed in the beam path under the control of an actuator 94 which is configured to displace two filter plates 92 and 93 as indicated by an arrow 95. The filter plates 92 and 93 differ with respect to a polarization of the light which is allowed to traverse the respective plate. For example, the filter plate 92 allows light polarized to 80% in a first direction to pass through, whereas the filter plate 93 allows light polarized to 80% in a second direction orthogonal to the first direction to pass through. It is to be noted that such effect can be also achieved with one single polarizing filter plate and an actuator configured to rotate the filter plate about an axis parallel to an optical axis of the imaging beam path traversing the plate.

The spectral filter 91 comprises two filter plates 96 and 97 which can be selectively placed in the beam path under the control of an actuator 98 which is configured to displace two filter plates 96 and 97 as indicated by an arrow 99. The filter plates 96 and 97 differ with respect to a wavelength range of the light which is allowed to traverse the respective plate. For example, the filter plate 96 allows only light from within a wavelength range from 410 nm to 450 nm with a central wavelength of 430 nm to pass through, whereas the filter plate 97 allows only light from within a wavelength range from 630 nm to 670 nm with a central wavelength of 650 nm to pass through.

According to other examples of the system 31 illustrated in FIG. 1, the optical filter includes only a polarizing filter while a spectral filter is not provided, or the optical filter includes only a spectral filter while a polarizing filter is not provided, or the system does not include an optical filter in the imaging beam path at all.

According to other examples of the system 31 illustrated in FIG. 1 will have plural light sources generating light of different spectral distributions. For example, the plural light sources may include light emitting diodes (LEDs) generating light of different spectral distributions. The light sources can be selectively switched on and off to generate an illumination light beam having a selectable spectral distribution of its intensity.

The beam splitter 51 has a function of separating the imaging beam path 39 from a bright field illumination beam path 59. The bright field illumination beam path 59 comprises a bright field light source 61, a collimating lens 63 which may comprise one or more single lens elements and a mirror 65. The light source 61 is in this exemplary embodiment a xenon-arc lamp having a power of 35 W and emitting light in a broad spectral range. The lamp has a window having a function of an IR filter such that light having wavelength above 800 nm is substantially not transmitted towards the wafer 35. The light reflected from the mirror 65 is coupled into an optical fiber 67.

The bright field illumination light emerging from the optical fiber 67 is collimated by a lens group 69 and reflected from two mirrors 70, 71 before it enters an optical element group 73. The group 73 has a function of shaping the bright field illumination light beam such that an aperture 75 is homogenously illuminated. For this purpose, the lens group 73 comprises lenses and one or more optical integrators which may comprise fly eye lenses and/or glass rods. The aperture 75 is a field aperture and defines the portion of the object plane 37 which is illuminated with bright field illumination light. To achieve this, the bright field illumination optics is configured such that the field aperture 75 is imaged onto the wafer surface 33 which coincides with the object plane 37 of the imaging beam path. The bright field illumination light having traversed the field aperture 75 is manipulated by a lens group 77, reflected from a mirror 79, traverses the beam splitter 51 and the lens group 49, is reflected from the mirror 47 and traverses the objective lens 45 to be incident on the object plane 37.

The example of the system 31 illustrated in FIG. 1 further comprises optical filter 88 positioned in the illumination beam path extending from the light source 61 the wafer 35. The optical filter 88 can be used to select properties of the illumination light directed onto the wafer and, thus, also properties of the light used for the imaging of the wafer onto the array of pixels.

In the illustrated example, the optical filter 88 has a same configuration as the optical filter 89 positioned in the imaging beam path.

According to other examples, the optical filter 88 includes only a polarizing filter while a spectral filter is not provided, or the optical filter includes only a spectral filter while a polarizing filter is not provided, or the system does not include an optical filter in the imaging beam path at all. In particular, it is often sufficient to provide only one filer in either one of the illumination beam path and the imaging beam path. Herein it is possible that a polarization filter is only positioned in the illumination beam path while a spectral filter is only provided in the imaging beam path, or that a spectral filter is only positioned in the illumination beam path while a polarization filter is only provided in the imaging beam path.

In the embodiment shown in FIG. 1, the beam splitter 51 is traversed by the bright field illumination beam path 59, while the imaging beam path 39 is reflected from the beam splitter 51.

Figure 2:
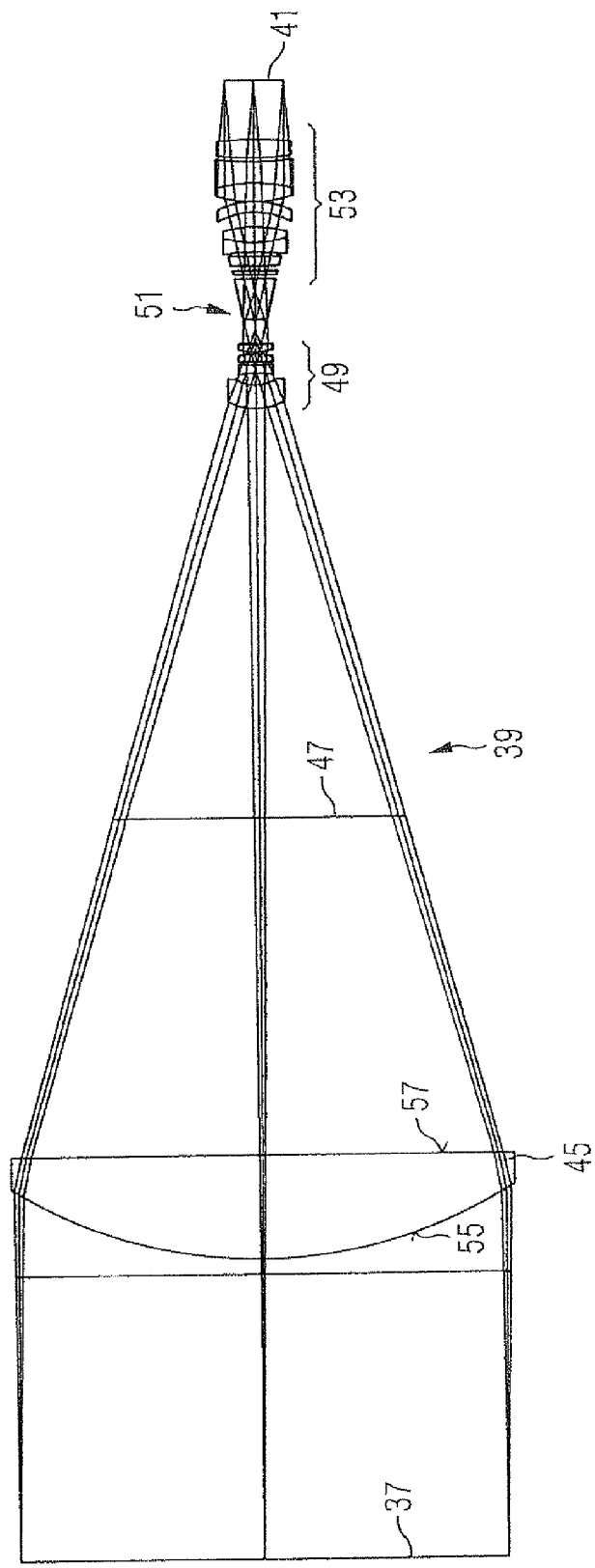
FIG. 2 is a schematic illustration of an imaging beam path of the inspection system shown in FIG. 1.

FIG. 2 is a more detailed, schematic illustration of the imaging optics 39, and optical data of the components of the imaging beam path 39 are shown in Table 1 below, wherein the column "glass" indicates optical materials according to the nomenclature of SCHOTT and OHARA:

TABLE 1

| Surf | Type | Radius Of curvature [mm] | Thickness [mm] | Glass | Free Diameter [mm] | Comment |
|---|---|---|---|---|---|---|
| OBJ | STANDARD | Infinity | 174 | | 301 | |
| 1 | STANDARD | Infinity | 10 | | 308.0416 | Additional Surface |
| 2 | COORDBRK | — | 0 | | — | Element Tilt |
| 3 | STANDARD | 305.3 | 62 | N-BK7 | 310.159 | |
| 4 | STANDARD | Infinity | −62 | | 302.9163 | |
| 5 | COORDBRK | — | 62 | | — | Element Tilt |
| 6 | STANDARD | Infinity | 208.56 | | 302.9163 | Max = 465 |
| 7 | STANDARD | Infinity | 256.39 | | 182.858 | 1. Mirror |
| 8 | STANDARD | 29.322 | 14.06995 | N-SSK5 | 32.44716 | |
| 9 | STANDARD | 21.596 | 7.110291 | | 22 | |
| 10 | STANDARD | −39.383 | 5.592504 | LAFN7 | 20.21797 | |
| 11 | STANDARD | 76.351 | 2.138976 | | 19.38703 | |
| 12 | STANDARD | −73.124 | 5.813038 | N-LAK14 | 19.38848 | |
| 13 | STANDARD | −45.479 | 0.6421531 | | 20.01052 | |
| 14 | STANDARD | 63.096 | 5.149779 | N-LAK10 | 19.71157 | |
| 15 | STANDARD | −73.918 | 14.5 | | 18.95065 | 311, 4 |
| STO | STANDARD | Infinity | 25 | | 14.60514 | 2. Beam Splitter |
| 17 | STANDARD | Infinity | 3 | | 26.64142 | Color Wheel |
| 18 | STANDARD | Infinity | 2.2 | BK7 | 28.14084 | Filter |
| 19 | STANDARD | Infinity | 3 | | 28.84776 | Color Wheel |
| 20 | STANDARD | Infinity | 6 | | 30.34717 | shutter |
| 21 | STANDARD | Infinity | 3 | | 33.346 | |
| 22 | STANDARD | −91.398 | 5.764071 | LLF1 | 34.04609 | |
| 23 | STANDARD | 112.61 | 10.73259 | N-PSK53 | 38.14386 | |
| 24 | STANDARD | −37.449 | 8.541288 | | 39.58976 | |
| 25 | STANDARD | −31.396 | 4.996902 | SF1 | 39.02309 | |
| 26 | STANDARD | −59.352 | 0.09566185 | | 43.5983 | |
| 27 | STANDARD | 60.213 | 12.15615 | N-SSK5 | 47.8217 | |
| 28 | STANDARD | −85.976 | 13.22124 | N-KZFS4 | 47.45478 | |
| 29 | STANDARD | 132.4 | 3.395106 | | 45.3592 | |
| 30 | STANDARD | 232.91 | 9.686887 | LAFN7 | 45.44828 | |
| 31 | STANDARD | −359.96 | 1 | | 44.92545 | |
| 32 | STANDARD | Infinity | 36.02343 | | 44.55453 | Fix 31 |
| IMA | STANDARD | Infinity | | | 36.78733 | |

Figure 3:
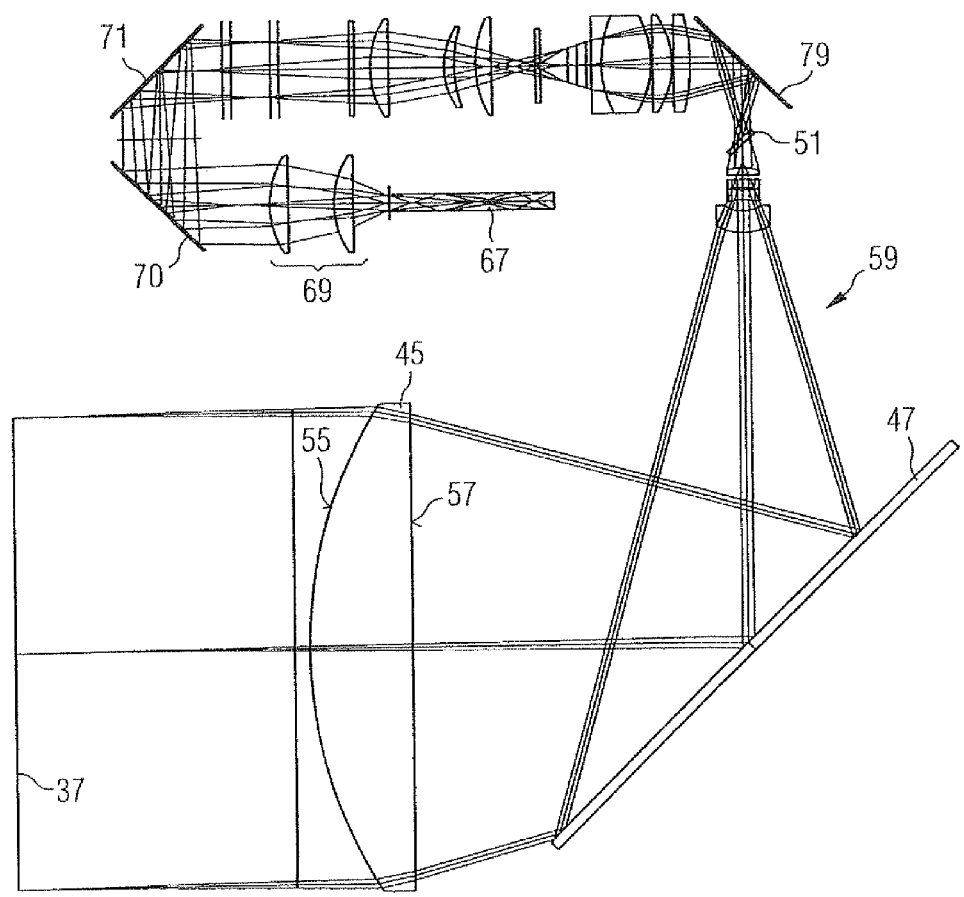
FIG. 3 is a schematic illustration of an illuminating beam path of the inspection system shown in FIG. 1.

FIG. 3 is a detailed illustration of the bright field illumination beam path, wherein components of the bright field illumination system upstream of the optical fiber 67 are not shown in FIG. 3.

Optical data of the components included in the bright field illumination system are shown in Table 2 below:

TABLE 2

| Surf | Type | Radius Of curvature [mm] | Thickness [mm] | Glass | Free Diameter [mm] | Comment |
|---|---|---|---|---|---|---|
| OBJ | STANDARD | Infinity | 174 | | 296 | |
| 1 | STANDARD | Infinity | 10 | | 302.4957 | Additional Surface |
| 2 | COORDBRK | — | 0 | | — | Element Tilt |
| 3 | STANDARD | 305.3 | 62 | N-BK7 | 304.3861 | |
| 4 | STANDARD | Infinity | −62 | | 296.6796 | |
| 5 | COORDBRK | — | 62 | | — | Element Tilt |
| 6 | STANDARD | Infinity | 208.56 | | 296.6796 | Max = 465 |
| 7 | COORDBRK | — | 0 | | — | |
| 8 | STANDARD | Infinity | 0 | MIRROR | 352.6987 | 1. Mirror |
| 9 | COORDBRK | — | −256.39 | | — | |
| 10 | STANDARD | −29.322 | −14.06995 | N-SSK5 | 31.88391 | |
| 11 | STANDARD | −21.596 | −7.110291 | | 22 | |
| 12 | STANDARD | 39.383 | −5.592504 | LAFN7 | 19.78167 | |
| 13 | STANDARD | −76.351 | −2.138976 | | 18.96394 | |
| 14 | STANDARD | 73.124 | −5.813038 | N-LAK14 | 18.95843 | |
| 15 | STANDARD | 45.479 | −0.6421531 | | 19.52432 | |
| 16 | STANDARD | −63.096 | −5.149779 | N-LAK10 | 19.23332 | |
| 17 | STANDARD | 73.918 | −14.5 | | 18.46875 | 311, 4 |
| 18 | COORDBRK | — | 0 | | — | |
| STO | STANDARD | Infinity | −3 | BK7 | 19.68119 | 1. Beam Splitter |
| 20 | STANDARD | Infinity | 0 | | 16.37627 | |
| 21 | COORDBRK | — | 0 | | — | |
| 22 | STANDARD | Infinity | −50 | | 30 | |
| 23 | COORDBRK | — | 0 | | — | |
| 24 | STANDARD | Infinity | 0 | MIRROR | 75 | |

TABLE 2-continued

| Surf | Type | Radius Of curvature [mm] | Thickness [mm] | Glass | Free Diameter [mm] | Comment |
|---|---|---|---|---|---|---|
| 25 | COORDBRK | — | 0 | | — | |
| 26 | STANDARD | Infinity | 30 | | 28.3432 | |
| 27 | STANDARD | 95.964 | 10.6 | BK7 | 60 | 01LPX263 |
| 28 | STANDARD | Infinity | 1 | | 60 | |
| 29 | STANDARD | 51.872 | 12.5 | BK7 | 60 | 01LPX183 |
| 30 | STANDARD | Infinity | 1 | | 60 | |
| 31 | STANDARD | 69.027 | 31 | N-BAF10 | 60 | 01LAO815 |
| 32 | STANDARD | −55.96 | 7 | SF11 | 60 | |
| 33 | STANDARD | −315.303 | 2 | | 60 | |
| 34 | STANDARD | Infinity | 6 | | 28.86784 | field mask if needed |
| 35 | STANDARD | Infinity | 6 | | 24.48367 | Rim mask |
| 36 | STANDARD | Infinity | 16.5 | | 21.66792 | field mask if needed |
| 37 | STANDARD | Infinity | 3 | BK7 | 46 | Mlk Polfilter |
| 38 | STANDARD | Infinity | 11 | | 46 | |
| 39 | STANDARD | Infinity | 16.2 | | 8.021884 | Irisblende |
| 40 | STANDARD | Infinity | 10.6 | BK7 | 60 | |
| 41 | STANDARD | −62.247 | 12 | | 60 | 01LPX209 |
| 42 | STANDARD | −90 | 7 | BK7 | 50 | |
| 43 | STANDARD | −42.52 | 33.3 | | 50 | 33.27 |
| 44 | STANDARD | Infinity | 12.5 | BK7 | 60 | |
| 45 | STANDARD | −51.872 | 10 | | 60 | |
| 46 | STANDARD | Infinity | 2.2 | BK7 | 58 | UV Filter/Masks |
| 47 | STANDARD | Infinity | 43.2 | | 58 | |
| 48 | STANDARD | Infinity | 5 | | 60 | array if needed |
| 49 | STANDARD | Infinity | 25 | | 60 | |
| 50 | STANDARD | Infinity | 5 | | 60 | array if needed |
| 51 | STANDARD | Infinity | 0 | | 60 | |
| 52 | STANDARD | Infinity | 40 | | 34.40161 | |
| 53 | COORDBRK | — | 0 | | — | |
| 54 | STANDARD | Infinity | 0 | MIRROR | 90 | KL mirror 74, 6 × 6 |
| 55 | COORDBRK | — | 0 | | — | |
| 56 | STANDARD | Infinity | −42.25 | | 38.52066 | |
| 57 | STANDARD | Infinity | −42.25 | | 50 | |
| 58 | COORDBRK | — | 0 | | — | |
| 59 | STANDARD | Infinity | 0 | MIRROR | 75 | |
| 60 | COORDBRK | — | 0 | | — | |
| 61 | STANDARD | Infinity | 5 | | 47.42887 | |
| 62 | STANDARD | Infinity | 63.2 | | 47.95598 | |
| 63 | STANDARD | 51.872 | 12.5 | BK7 | 60 | f 156 mm |
| 64 | STANDARD | Infinity | 26 | | 60 | |
| 65 | EVENASPH | 51.872 | 12.5 | BK7 | 60 | f 100 mm |
| 66 | STANDARD | Infinity | 22 | | 60 | |
| 67 | STANDARD | Infinity | 1 | | 20 | Rod start |
| 68 | NONSEQCO | Infinity | 0 | | 30 | |
| 69 | STANDARD | Infinity | 5 | | 10 | |
| IMA | STANDARD | Infinity | | 10 | | Rod end |

The bright field illumination system is configured to substantially homogenously illuminate the wafer surface 33 with bright field illumination light.

Figure 4:
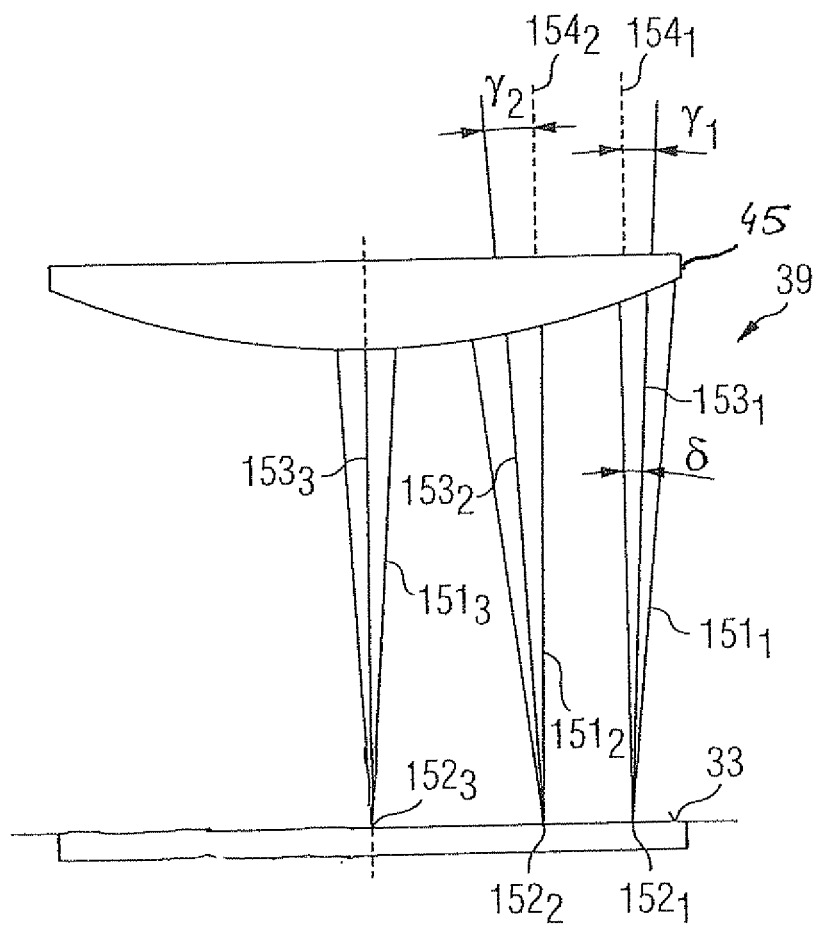
FIG. 4 is an illustration of a telecentric imaging.

FIG. 4 is a schematic illustration of geometric relations relating to numerical apertures and telecentric properties of the imaging beam path 39. FIG. 4 shows three light cones $151_1$, $151_2$, $151_3$ originating from three exemplary locations $152_1$, $152_2$, $152_3$ on the wafer surface 33. While light is emitted from those locations 152 into substantially all directions in the half space above the wafer surface 33, only those light rays which are within the cones 151 are accepted by the imaging optics and used for imaging of the wafer surface onto the array 41 of pixels of the detector 43. The sine of the half opening angle δ of the light cones 151 is also referred to as the numerical aperture NA on the object side of the imaging optics. In the illustrated embodiment, the numerical aperture NA of the imaging optics has a value of about 0.015.

FIG. 4 also shows angles γ between chief rays 153 of the light cones 151 and surface normals 154 of the wafer surface 33. The imaging optics of the present embodiment has a telecentric property such that a maximum value of angles γ for all light cones 151 used for imaging is less than about 4°.

Figure 5:
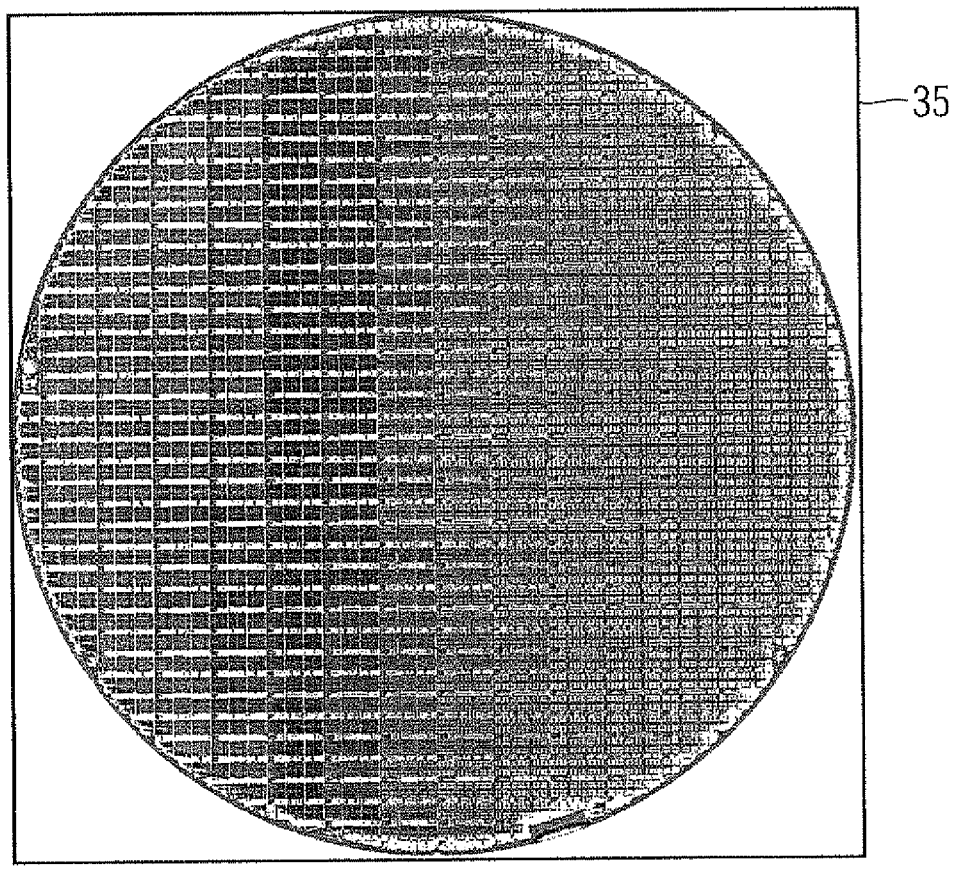
FIG. 5 is a representation of an image of a semiconductor wafer.

FIG. 5 shows an image of a patterned semiconductor wafer obtained with the inspection system illustrated with reference to FIGS. 1 to 4 above. The wafer 35 has a diameter of about 300 mm, and the image represents detection signals collected from the pixels of detector 43, wherein dark portions of the image represent low intensities of the detection signals and the bright portions of the image represent high intensities of the detection signals. The pixels of the detector are arranged in a two-dimensional 3000×3000 array totalling in 9 million pixels. With such an arrangement, an area of about 100 μm×100 μm on the wafer is imaged onto one pixel of the detector or, in other words, each pixel of the image represents an intensity of light collected from an area of about 100 μm×100 μm of the wafer 35.

The patterns on the wafer are formed of plural identical exposure fields, each generated in one exposure step.

Figure 6:
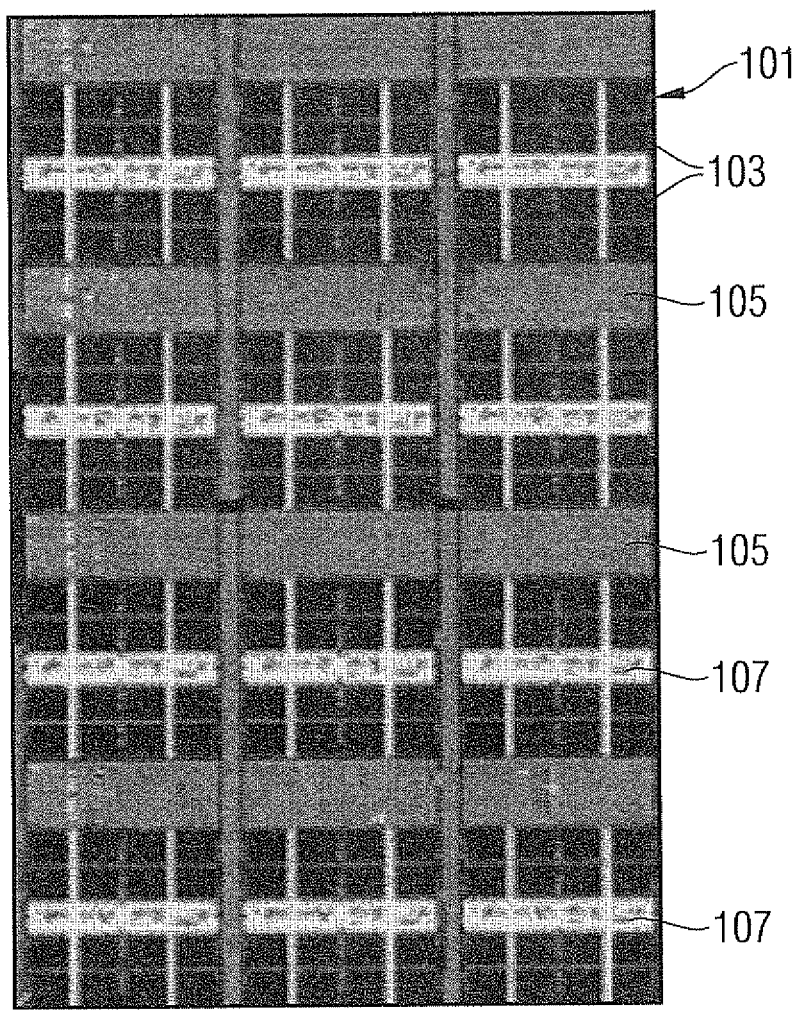
FIG. 6 is an image of an exposure field of the wafer shown in FIG. 5.

FIG. 6 is an enlarged view of one such exposure field 101 which has a horizontal extension of 26 mm and a vertical extension of 33 mm. In the illustrated example, the exposure field 101 corresponds to one die which will, upon completion of the manufacture of the wafer form one functional semiconductor circuit or chip. It is apparent from FIG. 6 that the die has different types of regions, such as black regions, grey regions and white regions arranged in a manhattan pattern. The different regions correspond to different arrangement patterns of microstructures formed on the wafer substrate. The black regions 103 of the image correspond to regions on the wafer where a semiconductor memory is formed, the grey regions 105 of the image correspond to regions on the wafer where main logic support structures are formed, and the bright regions 107 of the image correspond to regions on the wafer where logic sub-structures are formed. The semiconductor memory regions 103 are formed by microstructures arranged in a highly regular repetitive arrangement pattern with a smallest repetition period of about 70 nm in the horizontal and vertical directions.

Figure 7:
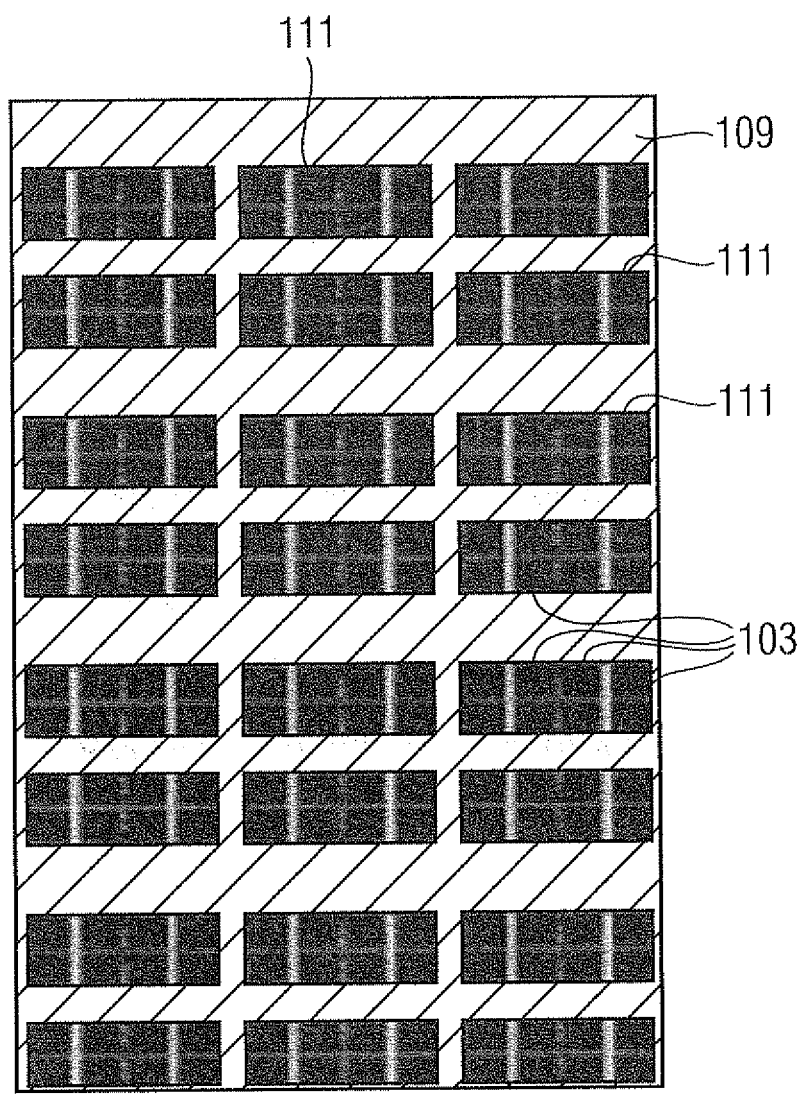
FIG. 7 is a schematic illustration of a mask which can be overlayed on the image shown in FIG. 6.

The memory regions 103 are selected for further analysis by applying a mask 109 shown in FIG. 7 as hatched portions. The mask 109 covers the horizontal and vertical portions of the grey regions 105 and the horizontal portions of the bright regions 107 shown in FIG. 6. The portions of the image 101 coinciding with the mask 109 are excluded from the further analysis. The further analysis is directed to each of those portions of the image 101 coinciding with a window or opening 111 of the mask 109. Those pixels of the image corresponding to one opening 111 of the mask are each grouped into a selected group of pixels, wherein one or more measurement values are calculated from each selected group of pixels. In the illustrated example, one single value is calculated by averaging the image intensities of the pixels of each group. Since the mask 109 shown in FIG. 7 has 3×8 openings 111, 24 values are calculated for each exposure field 101 of the wafer 35.

The following table 3 shows an example of such values obtained for an exemplary exposure field as shown in FIG. 6.

TABLE 3

| 1860 | 1828 | 1845 |
| 1884 | 1852 | 1869 |
| 2164 | 2123 | 2134 |
| 2105 | 2080 | 2110 |
| 2013 | 2012 | 1988 |
| 1887 | 1847 | 1880 |
| 1846 | 1817 | 1820 |
| 1835 | 1819 | 1828 |

It is apparent that the averaged intensity values are not identical for all of the selected regions of the wafer corresponding to the respective windows 111, even though the microstructures formed in the respective memory regions are expected to be the same. It is to be noted that it is not possible to directly image the microstructures with the inspection system of FIG. 1 using the detector with 9 million pixels since the microstructures are much smaller than the area of 100 μm×100 μm imaged onto one pixel of the detector.

It has been found that the averaged intensity values shown in the table above are indicative of variations of feature properties of the microstructures in the different selected regions 111. Those feature properties are not perfectly identical for all regions 111 of the exposure field. In fact, the feature properties are slightly varied from region to region. It has been found that already slight variations of the feature properties result in noticeable differences of the averaged values as shown in Table 3 above.

In the illustrated example, the variations of the averaged values are attributed to variations of a critical dimension with which the microstructures are formed on the wafer. In other examples, the variations of feature properties which correspond to variations of the averaged values may comprise a line width, a side wall angle, a height, a footing, an undercut and a corner rounding of features of microstructures, an overlay shift between structures of a current or top layer relative to structures of a preceeding layer covered by the top layer, and layer thicknesses of the features of the microstructures or other feature properties.

In the illustrated example, one value is calculated by averaging of the detection signals collected from one group of pixels. In other examples, one value or plural values can be calculated by other mathematical operations from the selected group of detection signals. The mathematical methods may comprise a statistic analysis, a determination analysis, a calculation of an average, a calculation of a median, a calculation, of a variance, a calculation of a standard deviation. These one or more calculated values can be again indicative of variations of feature properties of the microstructures formed on the substrate. However, it is to be noted that the number of values calculated from a selected group of pixels is less than the number of pixels in the group. For example, the number of pixels in the group can be greater than 5 or greater than 10, while the number of values calculated from the group is less than 5 or equal to 1. According to another example, the number of pixels in the group is greater than 40, while the number of values calculated from the group is less than 10 or, in particular, equal to 1.

In the example illustrated with reference to FIG. 7, the mask covers the horizontal and vertical portions of the grey regions 105 and the horizontal portions of the bright regions 107, while the narrow vertical portions of the white regions are not completely covered by the mask. The mask can be further improved by also covering the narrow vertical portions of the bright regions 107, such that each group of pixels corresponding to a window in the mask would correspond to exactly one memory portion of the wafer. In other examples, other shapes of the mask can be found which would also allow to obtain values which are indicative for feature properties of microstructures formed in selected regions of the substrate.

Figure 8:
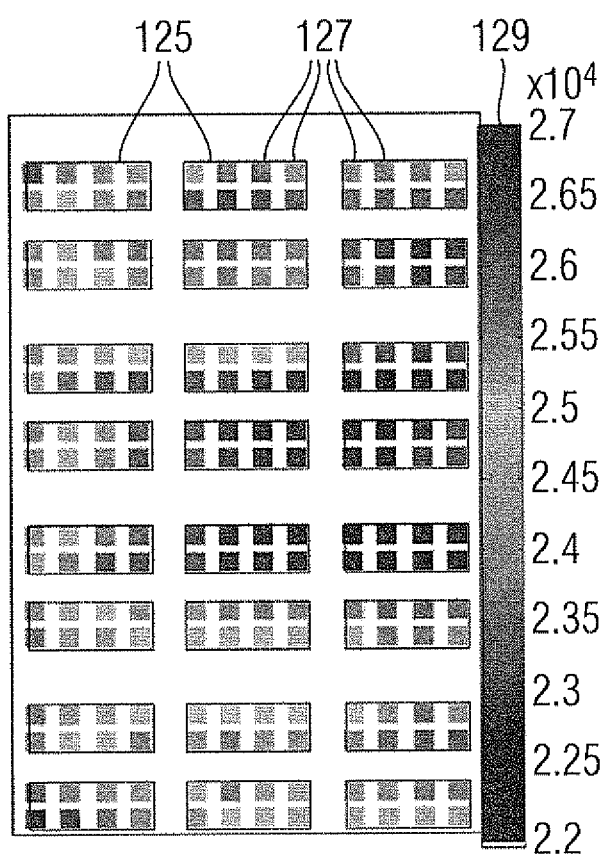
FIG. 8 is a schematic illustration of an intermediate result of a calculation.

FIG. 8 shows a result of a processing using a mask, wherein each window in the mask corresponds to exactly one memory portion of the wafer 35. Rectangles 125 in FIG. 8 correspond to the windows 111 of the mask 109 shown in FIG. 7. In this illustrated example, however, the mask comprises windows represented by shaded rectangles 127 in FIG. 8. Each window of this mask corresponds to one memory portion 103 of the wafer 35. For each such window of the mask, a processing with groups of pixels is performed as illustrated above, wherein one result value is calculated from each group of pixels. The result value is represented in FIG. 8 as a grey value of the shaded rectangles, wherein a corresponding grey scale 129 is shown at the right side of FIG. 8.

Figure 9:
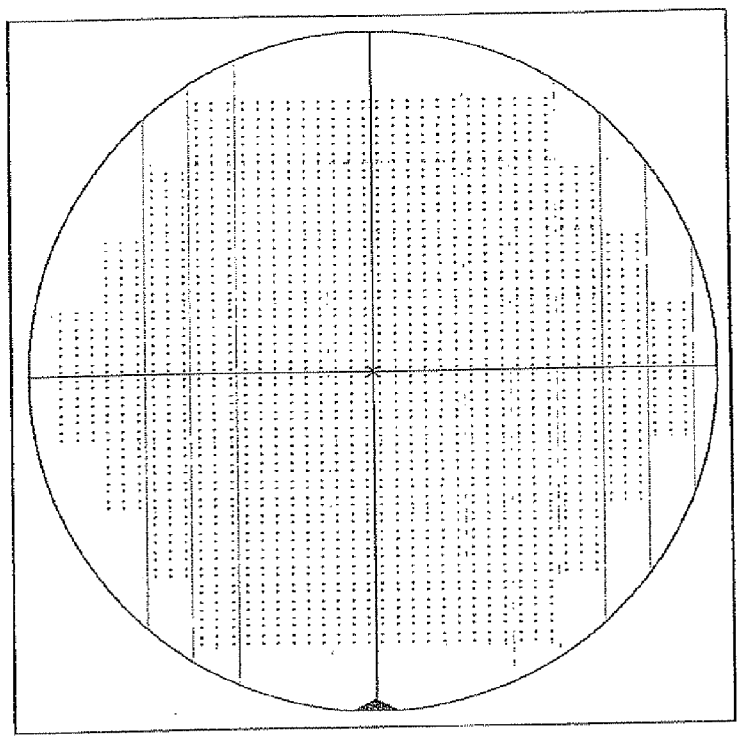
FIG. 9 is an illustration representing a correspondence between values calculated from the image shown in FIG. 5 and selected regions of the semiconductor wafer.

FIG. 9 is a representation of a correspondence between calculated values and their corresponding regions on the wafer. Each point in FIG. 8 represents one value corresponding to one selected region on the wafer, and it is apparent that for each exposure field there are calculated 24 values by averaging as illustrated above and wherein 88 complete exposure fields are formed on the wafer. The 2112 values are indicative for feature properties, such as a critical dimension, in 2112 different selected regions of the wafer. The number of 2112 values, each indicative of a feature property of the microstructures formed in the selected regions, is a relatively low number of information as compared to the information generated by a micro-inspection system which is conventionally necessary to obtain comparable information of the microstructures. If a micro-inspection tool was used for obtaining information about feature properties at 2112 locations on the wafer, the micro-inspection tool would have to perform detailed measurements at those 2112 locations which would be a time consuming process. In the present example, the information is obtained from one image of the wafer which can be collected in the order of about 10 seconds.

Figure 10:
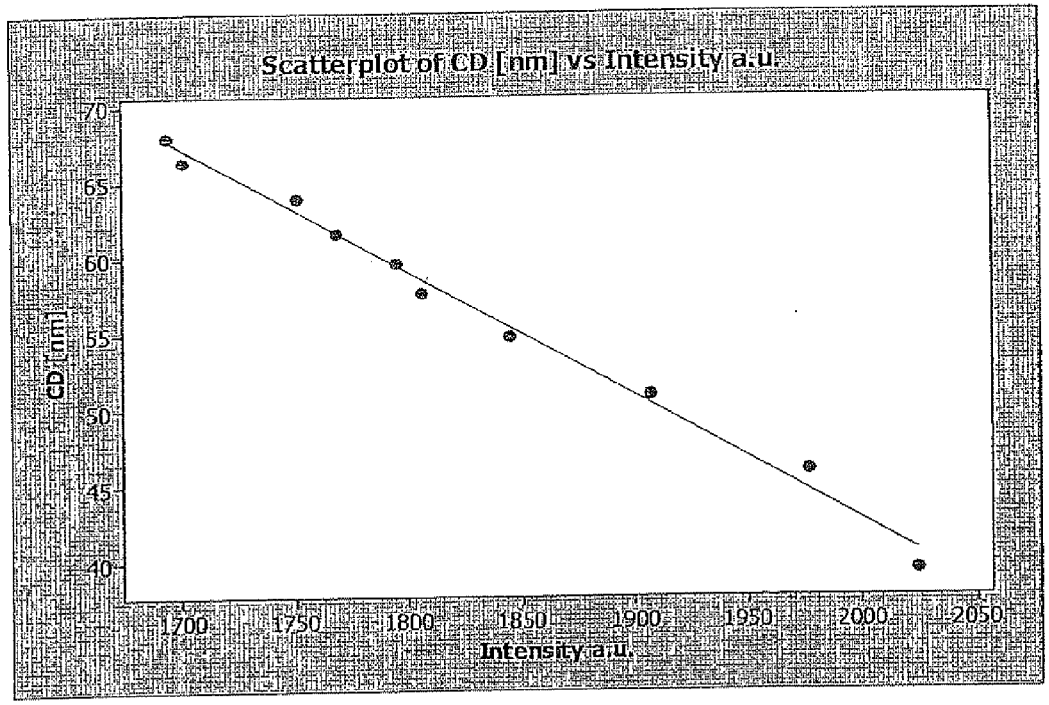
FIG. 10 shows a dependency of determined values from a critical dimension.

FIG. 10 is a graphical representation of measuring results obtained from a test wafer with the method illustrated above. The test wafer was manufactured such that a critical dimension of microstructures formed on the wafer is varied from exposure field to exposure field. 14 exposure fields are formed on the wafer with critical dimensions varying from 40 nm to 70 nm. For each exposure field, the corresponding pixels are selected to form groups, wherein the detection signals collected from each group are averaged. Each point in FIG. 10 corresponds to one such value associated with the manufactured critical dimension of the corresponding exposure field. It is apparent that the calculated values are highly correlated with the critical dimension of the microstructures. It is also apparent that valuable information relating to feature properties of the microstructures can be obtained using the macro-inspection tool in which an area on the wafer containing many microstructures is imaged onto one pixel of the detector.

Figure 11:
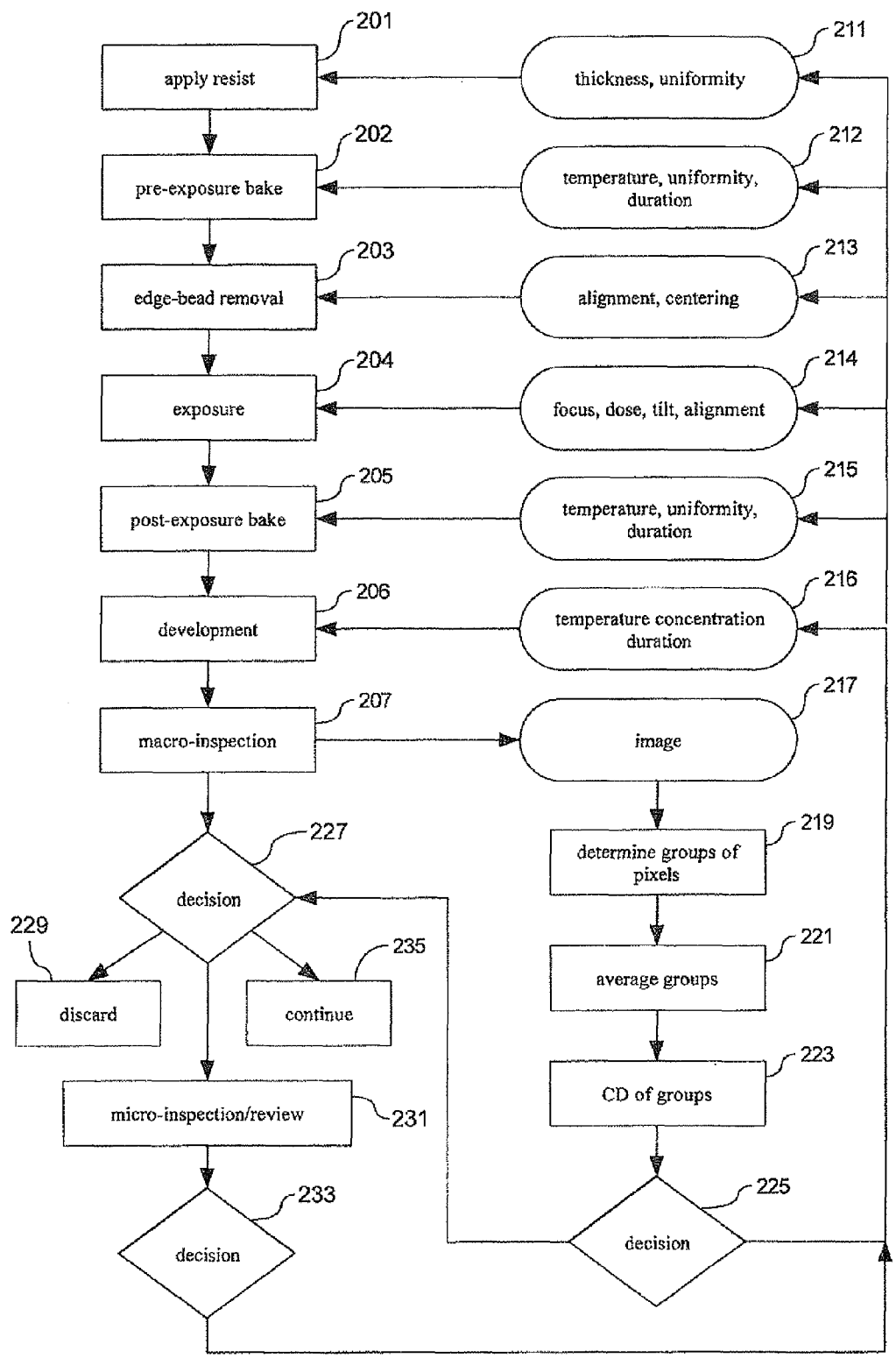
FIG. 11 is a flow chart illustrating a method of processing of a semiconductor wafer.

FIG. 11 illustrates a method of processing a semiconductor wafer. The method is performed at a litho-cluster which comprises a track system which coats and develops wafers with a resist, linked to a lithography system which images patterns onto a wafer. The method includes plural processing steps 201 to 206 and an inspection step 207. In step 201a resist layer is applied to the wafer surface, wherein this processing is controlled by process parameters 211, such as a thickness and a uniformity of the applied layer. In a step 202 the wafer undergoes a pre-exposure bake which is controlled by process parameters 212 such as a temperature, a temperature uniformity or a duration of bake. In a subsequent edge bead removal step 203, a portion of the resist layer covering the wafer edge is removed. This processing is controlled by process parameters 213, such as an alignment or centering of the wafer relative to a tool performing the removal of the resist. In a subsequent exposure step 204 the resist is exposed with a pattern, wherein the exposure is controlled by process parameters 214, such as a focus, an exposure dose and a tilt and an alignment of the wafer relative to an exposure tool. Thereafter, a post-exposure bake step 205 is performed, wherein this processing is controlled by process parameters 215, such as a temperature, a temperature uniformity and a duration. In a step 206, the resist is developed, wherein the development is controlled by process parameters 216 such as a temperature, a concentration of applied substances and a duration.

The inspection step 207 can be performed using the inspection tool and calculation methods illustrated above. The inspection 207 includes recording of an image 217 and image processing and calculating steps 219 to 223. In a step 219 a mask is applied to the image to exclude image signals from groups of pixels from the further processing. For example, the mask can be configured such that image portions corresponding to non-memory portions of the wafer are excluded from the further processing. In a step 221, the non-excluded portions of the image are grouped into blocks for which values are calculated by operations such as averaging. In a step 223 a feature property, such as a CD, is determined from the values calculated in step 221. After a feature property, such as a CD, is associated with each block in step 223, a decision step 225 is performed. The decision step 225 may include decisions directed to changing the process parameters 211 to 216 based on the determined feature properties. If necessary, the processed parameters are changed to improve the processing in steps 201 to 206 for next wafers undergoing the processing. The analysis performed in decision step 225 may also influence a decision 227 in which a determination is made whether the currently inspected wafer is discarded in a step 229 because the inspection 207 has revealed serious defects and deficiencies of the wafer. If the decision 227 finds that the currently inspected wafer fulfils certain design requirements, the wafer continues to undergo further processing steps 235 of its manufacture.

Since the inspection 207 uses a macro-inspection tool for obtaining information, such as a critical dimension or a line width or other information relating to feature properties of the formed microstructures, the inspection 207 can be performed very rapidly. The result of the inspection can be immediately used to decide on whether the wafer should be further processed or discarded. Further, the information can be used to improve the manufacturing process by changing process parameters controlling processing of following wafers.

In the example illustrated above, the inspection 207 is performed after the development 206. In other examples, the inspection is performed after other processing steps, such as the exposure 204, the pre-exposure bake 202, the application 201 of the resist layer or the post-exposure bake 205. Still further, the inspection can be performed after more than one or all of the processing steps to further improve the control of the individual processing steps.

The decision 227 may also include a decision to perform a micro-inspection and review in a step 231. The micro-inspection is an inspection using a micro-inspection tool which is capable of directly determining feature properties of the microstructures formed on the wafer. For this purpose, the micro-inspection tool has, for example, imaging optics providing a high imaging resolution. The micro-inspection of step 231 is performed at selected locations of the wafer, wherein those locations are determined based on the calculated values of, for example CD, of particular groups of pixels determined in step 223. For example, if the largest value of an averaged intensity of one group of selected pixels (see the maximum entry in Table 3 above) exceeds a predetermined threshold or is by a predetermined amount greater than values of other groups, this can be indicative of a deficiency in the selected region of the wafer corresponding to that group. It is then possible to direct the micro-inspection to that selected region, wherein time can be saved by not performing the micro-inspection at other regions for which the calculated values are within ranges which are indicative of feature properties which are within a desired range.

Based on results of the micro-inspection 231, a decision 233 can be made to change one or more of the process parameters 211 to 216 to improve the processing of other wafers.

Figure 12:
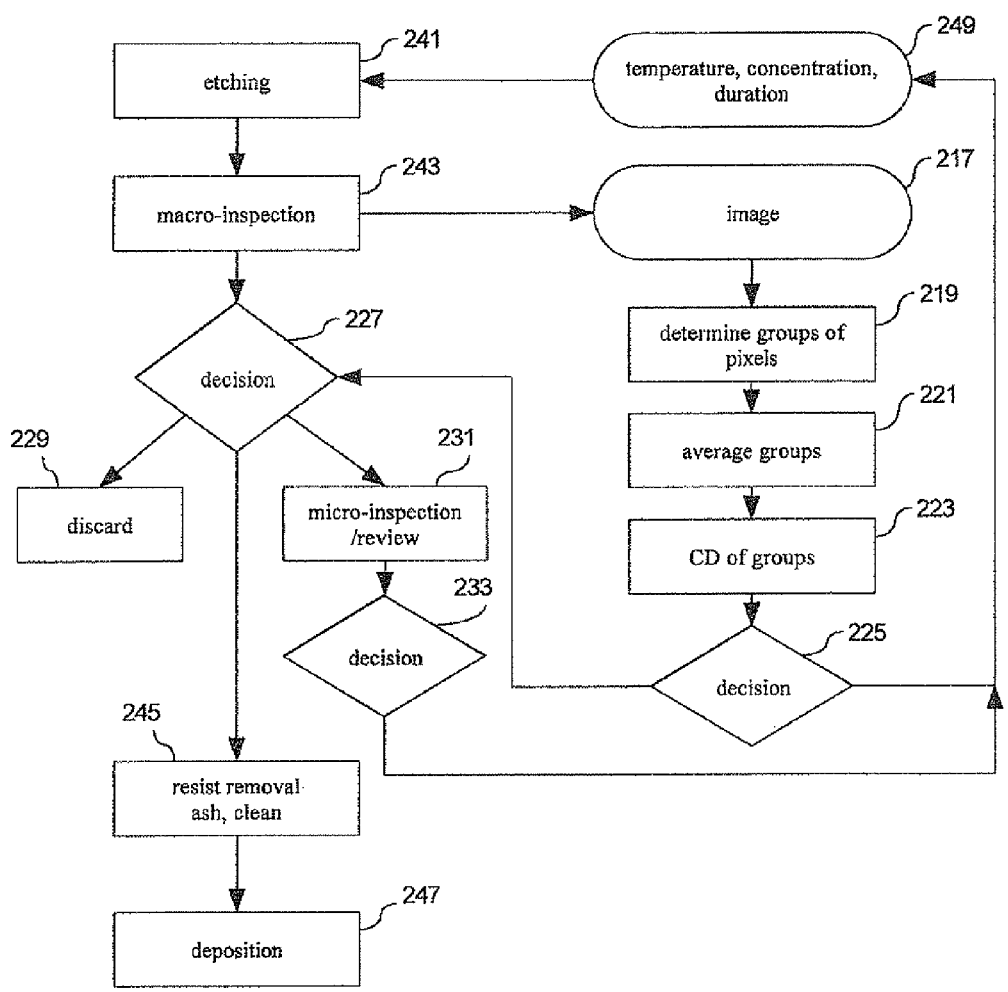
FIG. 12 is a flowchart illustrating a further method of processing of a semiconductor wafer.

FIG. 12 illustrates a further method of processing a semiconductor wafer. This method can be performed subsequent to the method illustrated with reference to FIG. 11 at the continuation step 235. The method illustrated in FIG. 12 can be performed at an etching and deposition process module used in a wafer manufacture. The method includes a processing step 241 in which the pattern of the developed resist is transferred to the wafer substrate by etching. The etching is controlled by process parameters 249, such as a temperature, a concentration and a duration of the processing.

After the etching, a macro-inspection 207 is performed to generate an image 217. A processing of the image 217 includes steps 219, 221 and 223 as illustrated above with reference to FIG. 11. Also decision steps 225 and 227 as already illustrated above are performed to discard 229 the wafer, perform a micro-inspection/review 231 as illustrated above and to perform a decision step 233 based thereon, or to continue with the manufacture of the wafer at a step 245, in which the developed resist remaining on the wafer is removed in an ash process and a cleaning process.

The decision in step 225 may also include changing the process parameters 249 determining the etching process 241 to improve manufacture of subsequent wafers. Similarly, the decision in step 225 may also include changing the process parameters 211 to 217 (see FIG. 11) determining the processing steps 201 to 206 as illustrated with reference to FIG. 11 to improve manufacture of subsequent wafers.

Figure 13:
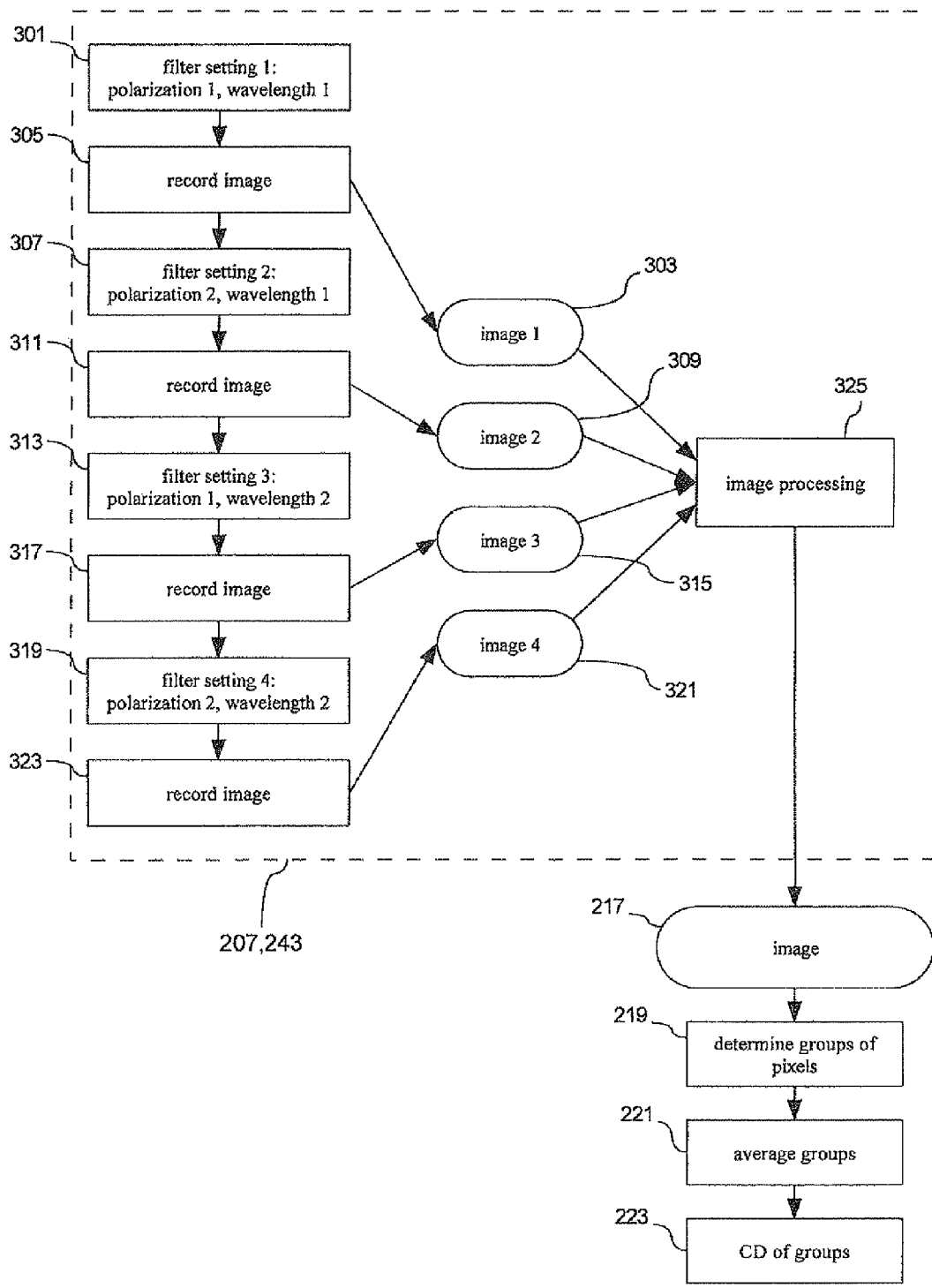
FIG. 13 is a flowchart illustrating a detail of an inspection which can be used in one of the methods illustrated in FIGS. 11 and 12.

FIG. 13 is a flowchart illustrating a detail of a embodiment of the inspection which can be used, for example, in step 207 of the method illustrated with reference to FIG. 11 or step 243 of the method illustrated with reference to FIG. 12.

In the method shown in FIG. 13, more than one image is recorded from a same wafer maintained at a same position relative to the inspection system used. The inspection system can be the inspection system illustrated above with reference to FIGS. 1 to 4, wherein other inspection systems having different configurations can be used as well. The plural recorded images differ with respect to a setting of the light used for illuminating the wafer and/or the light used for imaging the wafer. The different settings of the light may include settings with respect to a spectral distribution of the light and a polarization of the light. The settings can be selected with optical filters, such as the optical filters 88 and 98 illustrated above with reference to FIG. 1.

In a step 301, a first light setting is selected by controlling the actuators 94 and 98 of the filters 89 and 88, such that light of a first wavelength range from 410 nm to 450 nm and central wavelength of 430 nm polarized according to a first polarization direction can be used to record an image. A first image 303 is recorded using this setting in a step 305.

In a subsequent step 307, a second light setting is selected by controlling one of the filters 89 or 88, such that light of a the first wavelength range polarized according to a second polarization direction orthogonal to the first polarization direction can be used to record an image. A second image 309 is recorded using this setting in a step 311.

In a subsequent step 313, a third light setting is selected by controlling the filters 89 and 88, such that light of a second wavelength range from 630 nm to 670 nm and central wavelength of 650 nm polarized according to the first polarization direction can be used to record an image. A third image 315 is recorded using this setting in a step 317.

In a subsequent step 319, a fourth light setting is selected by controlling one of the filters 89 or 88, such that light of a the second wavelength range polarized according to the second polarization direction can be used to record an image. A fourth image 321 is recorded using this setting in a step 323.

The four recorded images 303, 309, 315, 321 undergo an image processing in a step 325 to calculate a new image 217. The new image 217 is calculated pixel by pixel, wherein pixel intensities of each pixel are calculated based on pixel intensities of corresponding pixels of each of the images 303, 309, 315, 321.

For example, the pixel intensity of pixels of the new image can be calculated according to the formula $$I_n = \frac{a_1 I_1}{a_2 I_2} - \frac{a_3 I_3}{a_4 I_4},$$

wherein $I_n$ is the pixel intensity of the pixel in the new image 217, $I_1$ is the pixel intensity of the pixel in the first image 303, $I_2$ is the pixel intensity of the pixel in the second image 309, $I_3$ is the pixel intensity of the pixel in the third image 315, $I_4$ is the pixel intensity of the pixel in the fourth image 321, and $a_1$, $a_2$, $a_3$ and $a_4$ are suitably chosen constants.

It has been found that an image formed of ratios of pixel intensities relating to different polarizations shows a high contrast for miniaturized structures of the wafer periodically arranged in a direction coinciding with one of the first and second polarization directions. The above formula represents a difference of such images recorded at different wavelengths. The first and second images are recorded at the longer wavelength where the light penetrates deeper into the wafer than the light of the shorter wavelength which is used to record the third and fourth images. The image calculated from the ratio $a_1 I_1/a_2 I_2$ is indicative of repetitive structures located at both the surface and in a certain depth below the surface of the wafer, while the image calculated from the ratio $a_3 I_3/a_4 I_4$ is indicative of repetitive structures located at the surface of the wafer only. Therefore, the image calculated using the formula above, which is a difference of the image indicative of repetitive structures located at both the surface and in a certain depth below the surface of the wafer, and the image indicative of repetitive structures located only at the surface of the wafer, is indicative of repetitive structures located in the certain depth below the surface of the wafer. The suitable constants $a_1$, $a_2$, $a_3$ and $a_4$ can be found by some experimentation and previous experience.

The image 217 calculated using the light settings as illustrated above has been helpful in identifying manufacturing defects in high aspect ratio structures formed in the semiconductor wafer. For example, gate contact holes in DRAM memory may have a diameter of 50 nm and a depth of 2000 nm. It may occur in DRAM manufacture that the some contact holes have a perfect shape at the surface of the wafer but have not been etched to their full depth. It would not be difficult to detect such defects using conventional surface inspection methods. However, such defects can be detected using the method illustrated above which provides information relating to structures located below the wafer surface.

While the first and second wavelength ranges in the example illustrated above are obtained by changing a setting of one of the optical filters provided in the illumination beam path or the imaging beam path, it is also possible to achieve the first and second wavelength ranges by providing two light sources, wherein a first light source generates the light of the first wavelength range and a second light source generates the light of the second wavelength range, and wherein only the first light source is switched on when the first and second light settings are selected and only the second light source is switched on when the third and fourth light settings are selected.

According to some embodiments, a wafer inspection method comprises imaging a full surface of the wafer at an imaging resolution insufficient to resolve individual microstructures which are repetitively arranged on the wafer. A mask is applied to the recorded image and unmasked portions of the image are further processed by averaging. The unmasked portions are selected such that they include memory portions of the wafer.

While certain exemplary embodiments are disclosed herein, alternatives, modifications and variations will be apparent to those skilled in the art. Accordingly, the exemplary embodiments set forth herein are intended to be illustrative and not limiting in any way. Various changes may be made without departing from the spirit and scope of the present disclosure.

What is claimed is:

1. A method comprising:
   imaging at least a portion of a substrate onto an array of pixels of a detector, wherein the substrate includes a plurality of regions in which microstructures are arranged according to different arrangement patterns and wherein in at least one selected region the microstructures are arranged according to a regular repetitive arrangement pattern having a repetition period, wherein an area of the substrate that is imaged onto one pixel of the detector has an extension of more than 5 times the repetition period, and wherein each selected region from the at least one selected region is imaged onto a group of selected pixels;
   collecting detection signals from pixels of the detector; and
   calculating at least one value for the group of selected pixels for each selected region using the detection signals from pixels that are members of the group of selected pixels, wherein detection signals from pixels that are not members of the group of selected pixels are not used in calculating the at least one value.

2. The method of claim 1, wherein each detection signal represents an intensity of light collected by a pixel.

3. The method of claim 1, wherein the calculating the at least one value for the group of selected pixels for each selected region includes a statistic analysis, a deterministic analysis, a calculation of an average, a calculation of a median, a calculation of a variance and a calculation of a standard deviation of the detection signals from pixels that are members of the group of selected pixels.

4. The method of claim 1, wherein a number of the values calculated for the group of selected pixels for each selected region is less than or equal to a number of the detection signals in the group of selected pixels divided by 9.

5. The method of claim 1, wherein a number of the detection signals in each group of selected pixels is greater than or equal to 9.

6. The method of claim 1, further comprising determining a feature property of the microstructures formed in the at least one selected region, wherein the feature property is determined based on the at least one value calculated for the group of selected pixels.

7. The method of claim 6, wherein the feature property comprises a line width, a side wall angle, a height, a footing, an undercut, a corner rounding and a critical dimension (CD), an overlay shift and a layer thickness of the microstructures arranged in the regular repetitive arrangement pattern.

8. The method of claim 1, wherein a plurality of selected regions in which the microstructures are arranged according to the regular repetitive arrangement pattern are provided on the substrate.

9. The method of claim 8, wherein the plurality of selected regions are arranged as a regular two-dimensional array.

10. The method of claim 9, wherein the substrate includes a plurality of dies, each die including at least one of the plurality of selected regions.

11. The method of claim 9, wherein the plurality of selected regions includes microstructures forming a semiconductor memory.

12. The method of claim 1, further comprising processing the substrate using at least one process parameter, and changing the at least one process parameter based on the at least one value calculated for the group of selected pixels for each selected region.

13. The method of claim 12, wherein the processing comprises at least one of:
   exposing the substrate with a pattern, wherein the at least one process parameter comprises an exposure dose and a focus used in the exposing;
   etching, wherein the at least one process parameter comprises an etch time, an etch temperature, and a concentration of a medium used in the etching;
   depositing material on the substrate, wherein the at least one process parameter comprises a concentration, a temperature and a duration.

14. The method of claim 12, wherein the processing comprises:
   coating the substrate with a resist;
   exposing a pattern onto the resist after the coating;
   developing the resist after the exposing;
   etching the substrate through the resist after the developing; and
   removing the resist remaining on the substrate after the etching;
   wherein the imaging at least the portion of the substrate, the collecting the detection signals and the calculating at least one value are performed after the etching of the substrate and before the removing of the resist.

15. The method of claim 1, wherein the imaging comprises imaging of all of the substrate onto the detector.

16. The method of claim 1, further comprising determining of at least one location on the substrate based on the at least one value and performing a micro-inspection of the at least on location.

17. The method of claim 1, wherein the imaging is a telecentric imaging such that a variation across the portion of the substrate of chief rays of an imaging beam path is less than 5°, and
   wherein the method further comprises illuminating the portion of the substrate wherein the illuminating is a telecentric illuminating such that a variation across the portion of the substrate of chief rays of an illuminating beam path is less than 5°.

18. The method of claim 1, wherein the imaging comprises a first imaging and a second imaging,
   wherein the first imaging is performed with radiation of a first polarization and the second imaging is performed with radiation of a second polarization different from the first polarization, and
   wherein the at least one value for the group of selected pixels for each selected region is calculated based on the detection signals collected in the first imaging and the second imaging.

19. The method of claim 18, further comprising:
   polarizing illumination light according to a first polarization direction;
   illuminating the substrate with the illumination light polarized according to the first polarization direction;
   performing the first imaging using the illumination light illuminated onto the substrate according to the first polarization direction;
   polarizing the illumination light according to a second polarization direction;
   illuminating the substrate with the illumination light polarized according to the second polarization direction; and
   performing the second imaging using the illumination light illuminated onto the substrate according to the second polarization direction.

20. The method of claim 18, further comprising:
polarizing imaging light used for imaging the portion of the substrate onto the array of pixels of the detector according to a first polarization direction;
performing the first imaging using the imaging light polarized according to the first polarization direction;
polarizing the imaging light according to a second polarization direction; and
performing the second imaging using the imaging light polarized according to the second polarization direction.

21. The method of claim 20, wherein the first polarization direction differs from the second polarization direction by more than 10°.

22. The method of claim 18, wherein the substrate is maintained in a same position relative to an imaging optics used in the imaging while performing the first imaging and the second imaging.

23. The method of claim 1, wherein the imaging comprises a first imaging and a second imaging,
wherein the first imaging is performed with radiation of a first wavelengths range and the second imaging is performed with radiation of a second wavelengths range different from the first wavelengths range, and
wherein the at least one value for the group of selected pixels for each selected region is calculated based on the detection signals collected in the first imaging and the second imaging.

24. The method of claim 23, further comprising:
limiting wavelengths of illuminating light to the first wavelength range;
illuminating the substrate with the illuminating light limited to the first wavelength range;
performing the first imaging using the illuminating light illuminated onto the substrate and limited to the first wavelength range;
limiting the wavelengths the illuminating light to the second wavelengths range;
illuminating the substrate with the illuminating light limited to the second wavelength range; and
performing the second imaging using the illuminating light illuminated onto the substrate and limited to the second wavelength range.

25. The method of claim 23, further comprising:
limiting imaging light used for imaging the portion of the substrate onto the array of pixels of the detector to the first wavelength range;
performing the first imaging using the imaging light limited to the first wavelengths range;
limiting the imaging light to the second wavelength range; and
performing the second imaging using the imaging light limited to the second wavelengths range.

26. The method of claim 23, wherein a central wavelength of the first wavelength range differs from a central wavelength of the second wavelength range by more than 50 nm.

27. The method of claim 23, wherein a width of each of the first wavelength range and the first wavelength range is smaller than 100 nm.

28. The method of claim 23, wherein a wavelength of 430 nm is within the first wavelength range.

29. The method of claim 23, wherein a wavelength of 650 nm is within the second wavelength range.

30. The method of claim 1, wherein the substrate includes miniaturized structures having an extension in a thickness direction of the substrate greater than 0.5 μm.

31. The method of claim 30, the miniaturized structures have an extension in a direction orthogonal to the thickness direction smaller than 0.1 times the extension in the thickness direction.

32. A method comprising:
positioning a substrate relative to an imaging optics and a camera such that the substrate is imaged onto the camera by the imaging optics;
directing illuminating light produced by a light source onto the substrate;
providing a first light setting of light used for imaging the substrate onto the camera and recording a first image of the substrate with the camera using illuminating light reflected from the substrate; and
providing a second light setting of light used for imaging the substrate onto the camera and recording a second image of the substrate with the camera using illuminating light reflected from the substrate;
wherein the first light setting and the second light setting differ with respect to at least one of a polarization and a spectrum of the illuminating light used for imaging the substrate onto the camera;
wherein a position of the substrate relative to the imaging optics and the camera is maintained constant between the recording of the first image and the recording of the second image.

33. The method of claim 32, wherein the first light setting and the second light setting are produced by at least one optical filter provided in a beam path between the light source and the substrate or between the substrate and the camera, wherein the at least one optical filter has a first setting different from a second setting with respect to at least one of the polarization and the spectrum of light traversing the at least one optical filter.

34. The method of claim 32, wherein the first light setting and the second light setting are produced by selectively operating different light sources producing illumination light of different spectral ranges.

35. The method of claim 32, wherein the illuminating light with which the first image is recorded has a first spectral distribution and the illuminating light with which the second image is recorded has a second spectral distribution, and wherein the first light setting and the second light setting are configured such that a central wavelength of the first spectral distribution differs from a central wavelength of the second spectral distribution by more than 50 nm.

36. The method of claim 35, wherein a width of each of the first spectral distributions and the second spectral distribution is smaller than 100 nm.

37. The method of claim 35, wherein a wavelength of 430 nm is within a width of the first spectral distribution and wherein a wavelength of 650 nm is within a width of the second spectral distribution.

38. The method of claim 32, wherein the illuminating light with which the first image is recorded has a first polarization direction and the illuminating light with which the second image is recorded has a second polarization direction, and wherein the first light setting and the second light setting are configured such that the first polarization direction differs from the second polarization direction by more than 10°.

39. The method of claim 32, including:
providing the first light setting and recording the first image of the substrate with the camera using illuminating light reflected from the substrate;
providing the second light setting and recording the second image of the substrate with the camera using illuminating light reflected from the substrate;

providing a third light setting and recording a third image of the substrate with the camera using illuminating light reflected from the substrate; and providing a fourth light setting and recording a fourth image of the substrate with the camera using illuminating light reflected from the substrate;

wherein the first light setting and the second light setting differ with respect to the polarization and are substantially the same with respect to the spectrum of the illuminating light used for imaging the substrate onto the camera;

wherein the third light setting and the fourth light setting differ with respect to the polarization and are substantially the same with respect to the spectrum of the illuminating light used for imaging the substrate onto the camera; and wherein the first light setting and the third light setting differ with respect to the spectrum of the illuminating light used for imaging the substrate onto the camera.

40. The method of claim 39, wherein a position of the substrate relative to the imaging optics and the camera is maintained constant between the recording of the first image, the second image, the third image, and the fourth image.

41. The method of claim 39, further comprising analyzing the first image, the second image, the third image, and the fourth image and obtaining information relating to miniaturized structures located below a surface of the substrate based on the first image, the second image, the third image, and the fourth image.

* * * * *